(12) United States Patent
Murase

(10) Patent No.: US 12,350,094 B2
(45) Date of Patent: Jul. 8, 2025

(54) INFORMATION PROCESSING APPARATUS, ULTRASOUND DIAGNOSTIC APPARATUS, INFORMATION PROCESSING METHOD, AND INFORMATION PROCESSING PROGRAM

(71) Applicant: FUJIFILM Corporation, Tokyo (JP)

(72) Inventor: Rito Murase, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 4 days.

(21) Appl. No.: 18/320,075

(22) Filed: May 18, 2023

(65) Prior Publication Data

US 2023/0293146 A1 Sep. 21, 2023

Related U.S. Application Data

(63) Continuation of application No. PCT/JP2021/042312, filed on Nov. 17, 2021.

(30) Foreign Application Priority Data

Nov. 27, 2020 (JP) .................... 2020-197656

(51) Int. Cl.
  *A61B 8/08* (2006.01)
  *A61B 8/00* (2006.01)
  *A61B 17/34* (2006.01)

(52) U.S. Cl.
  CPC .......... *A61B 8/0891* (2013.01); *A61B 8/461* (2013.01); *A61B 8/4245* (2013.01); *A61B 2017/3413* (2013.01)

(58) Field of Classification Search
  CPC ........ A61B 8/0891; A61B 8/0833–085; A61B 8/4245–4263; A61B 17/3403; A61B 2017/3413
  See application file for complete search history.

(56) References Cited

U.S. PATENT DOCUMENTS

2008/0195043 A1   8/2008  Schwach et al.
2008/0275396 A1  11/2008  Neerken et al.
(Continued)

FOREIGN PATENT DOCUMENTS

JP   2008-539932 A   11/2008
JP   2009-195585 A    9/2009
(Continued)

OTHER PUBLICATIONS

Ultrasound (www.nibib.nih.gov/science-education/science-topics/ultrasound, retrieved Sep. 27, 2024).*
(Continued)

*Primary Examiner* — Carolyn A Pehlke
(74) *Attorney, Agent, or Firm* — Studebaker Brackett PLLC

(57) ABSTRACT

An information processing apparatus includes an acquisition unit that acquires an ultrasound image of a vein in a predetermined region from a center to a periphery of a subject, a detection unit that detects an abnormal portion at which an abnormality occurs in the vein from the acquired ultrasound image, and a determination unit that determines whether a puncture in the vein is appropriate or inappropriate according to the detected abnormal portion, and outputs a determination result.

6 Claims, 8 Drawing Sheets

(56) References Cited

U.S. PATENT DOCUMENTS

| | | | |
|---|---|---|---|
| 2009/0259174 A1 | 10/2009 | Silver et al. | |
| 2010/0298705 A1* | 11/2010 | Pelissier | A61B 8/4254 600/443 |
| 2020/0338309 A1* | 10/2020 | Kopperschmidt | A61M 25/0116 |

FOREIGN PATENT DOCUMENTS

| | | |
|---|---|---|
| JP | 2018-000346 A | 1/2018 |
| WO | 2006/123282 A1 | 11/2006 |

OTHER PUBLICATIONS

International Search Report issued in PCT/JP2021/042312; mailed Jan. 25, 2022.
International Preliminary Report on Patentability (Chapter I) and Written Opinion of the International Searching Authority issued in PCT/JP2021/042312; issued May 30, 2023.

* cited by examiner

INFORMATION PROCESSING APPARATUS, ULTRASOUND DIAGNOSTIC APPARATUS, INFORMATION PROCESSING METHOD, AND INFORMATION PROCESSING PROGRAM

CROSS-REFERENCE TO RELATED APPLICATIONS

This application is a continuation application of International Application No. PCT/JP2021/042312, filed on Nov. 17, 2021, which is incorporated herein by reference in its entirety. Further, this application claims priority from Japanese Patent Application No. 2020-197656, filed on Nov. 27, 2020, the disclosure of which is incorporated by reference herein in their entirety.

BACKGROUND

Technical Field

The present disclosure relates to an information processing apparatus, an ultrasound diagnostic apparatus, an information processing method, and an information processing program.

Related Art

An ultrasound diagnostic apparatus that captures an ultrasound image of a subject using an ultrasound probe that receives an ultrasound echo by ultrasound transmitted toward the subject and outputs a reception signal based on the received ultrasound echo is known.

As technology of detecting an abnormality in a blood vessel by using the ultrasound image, for example, technology disclosed in JP2009-195585A and technology disclosed in JP2018-000346A are known. The technology disclosed in JP2009-195585A discloses the technology of specifying a position of a stenosis candidate in the blood vessel based on an area of a lumen of the blood vessel derived using volume data obtained by scanning a body surface of the subject with the ultrasound probe. In addition, JP2018-000346A discloses the technology of determining an abnormal part based on a blood flow in the blood vessel detected based on the ultrasound image of the subject.

SUMMARY

By the way, a blood vessel of the subject is punctured by inserting an insert, such as a so-called puncture needle or a catheter. As a puncture method, such as an echo-guided puncture method, a method is known in which the ultrasound image of the blood vessel of the subject is captured and a puncture is performed with reference to the blood vessel shown in the captured ultrasound image.

In a case in which the puncture is performed and an abnormality occurs in the blood vessel, it is necessary to consider the abnormality that occurs. According to the technology disclosed in JP2009-195585A and the technology disclosed in JP2018-000346A, the abnormal portion at which the abnormality occurs in the blood vessel can be presented to a user who performs the puncture, but a case in which the puncture is performed is not sufficiently considered.

The present disclosure has been made in view of the above circumstances, and provides an information processing apparatus, an ultrasound diagnostic apparatus, an information processing method, and an information processing program capable of performing assistance of a puncture position in consideration of the abnormality in the blood vessel with respect to the user who performs the puncture of the blood vessel.

A first aspect of the present disclosure relates to an information processing apparatus comprising an acquisition unit that acquires an ultrasound image of a vein in a predetermined region from a center to a periphery of a subject, a detection unit that detects an abnormal portion at which an abnormality occurs in the vein from the acquired ultrasound image, and a determination unit that determines whether a puncture in the vein is appropriate or inappropriate according to the detected abnormal portion, and outputs a determination result.

A second aspect of the present disclosure relates to the information processing apparatus according to the first aspect, in which the determination unit determines that a puncture at a position on a periphery side with respect to the abnormal portion is inappropriate.

A third aspect of the present disclosure relates to the information processing apparatus according to the first or second aspect, in which, in a case in which the detection unit detects a plurality of the abnormal portions, the determination unit determines that a puncture at a position on a periphery side with respect to an abnormal portion positioned on a most center side is inappropriate.

A fourth aspect of the present disclosure relates to the information processing apparatus according to any one of the first to third aspects, in which the acquisition unit further acquires a position of an ultrasound probe in a case in which the acquired ultrasound image is captured, and the determination unit determines whether the puncture is appropriate or inappropriate based on a detection result of the detection unit and the position of the ultrasound probe.

A fifth aspect of the present disclosure relates to the information processing apparatus according to any one of the first to fourth aspects, in which the determination unit outputs information indicating a warning as the determination result.

A sixth aspect of the present disclosure relates to the information processing apparatus according to any one of the first to fifth aspects, in which the detection unit detects the vein from the ultrasound image.

A seventh aspect of the present disclosure relates to an information processing apparatus comprising an acquisition unit that acquires an ultrasound image of a blood vessel in a predetermined region from a center to a terminal of a subject, a detection unit that detects an abnormal portion at which an abnormality occurs in the blood vessel from the acquired ultrasound image, and a determination unit that determines that a puncture of the blood vessel at a position at which a blood flow is upstream of the detected abnormal portion is inappropriate, and outputs a determination result.

An eighth aspect of the present disclosure relates to an ultrasound diagnostic apparatus comprising an ultrasound probe that receives an ultrasound echo from transmitted ultrasound, and outputs a reception signal based on the received ultrasound echo, an image generation unit that generates an ultrasound image based on the reception signal input from the ultrasound probe, and the information processing apparatus according to the present disclosure.

A ninth aspect of the present disclosure relates to an information processing method executed by a computer, the method comprising acquiring an ultrasound image of a vein in a predetermined region from a center to a periphery of a subject, detecting an abnormal portion at which an abnormality occurs in the vein from the acquired ultrasound image, and determining whether a puncture in the vein is appropriate or inappropriate according to the detected abnormal portion and outputting a determination result.

A tenth aspect of the present disclosure relates to an information processing program causing a computer to execute a process comprising acquiring an ultrasound image of a vein in a predetermined region from a center to a periphery of a subject, detecting an abnormal portion at which an abnormality occurs in the vein from the acquired ultrasound image, and determining whether a puncture in the vein is appropriate or inappropriate according to the detected abnormal portion and outputting a determination result.

According to the present disclosure, it is possible to perform assistance of a puncture position in consideration of the abnormality in the blood vessel with respect to the user who performs the puncture of the blood vessel.

DETAILED DESCRIPTION

Hereinafter, description of an embodiment of the present disclosure will be made in detail with reference to the drawings. It should be noted that the present embodiment does not limit the present disclosure.

Figure 1:
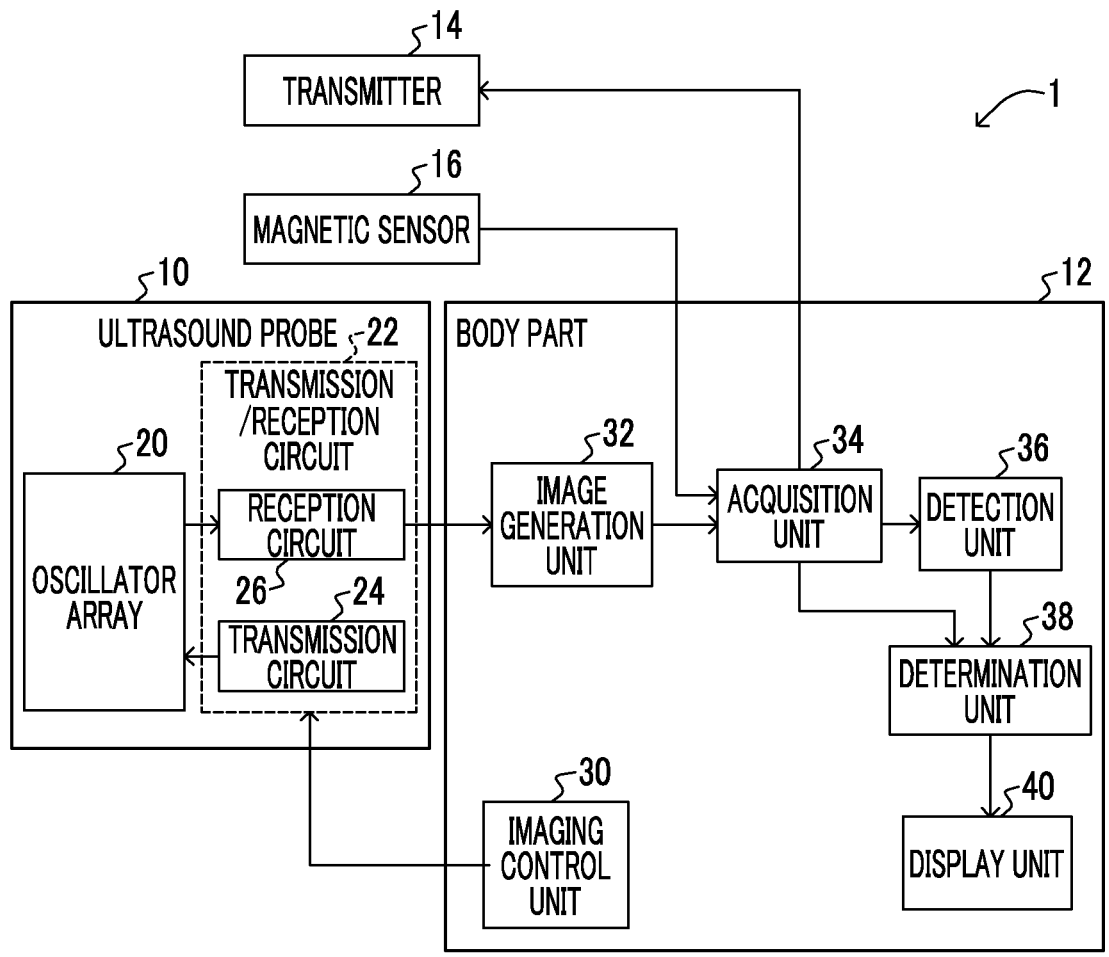
FIG. 1 is a block diagram showing an example of an overall configuration of an ultrasound diagnostic apparatus according to an embodiment.

First, an example of an overall configuration of an ultrasound diagnostic apparatus according to the present embodiment will be described. FIG. 1 shows a block diagram showing an example of an overall configuration of an ultrasound diagnostic apparatus 1 according to the present embodiment. As shown in FIG. 1, the ultrasound diagnostic apparatus 1 according to the present embodiment comprises an ultrasound probe 10 and a body part 12.

The ultrasound probe 10 comprises an oscillator array 20 and a transmission/reception circuit 22 including a transmission circuit 24 and a reception circuit 26. The oscillator array 20 comprises a plurality of oscillators (not shown) arranged in a one-dimensional or two-dimensional manner. As an example, in the present embodiment, a form will be described in which the ultrasound probe 10 is a linear-type ultrasound probe in which the plurality of oscillators are linearly arranged. It should be noted that the ultrasound probe 10 is not limited to the present form, and may be a convex-type or sector-type ultrasound probe in which oscillators are arranged in a curved manner. Each of the plurality of oscillators transmits ultrasound based on a drive signal applied from the transmission circuit 24, receives an ultrasound echo generated in a subject, and outputs an electrical signal according to the received ultrasound echo.

Each of the plurality of oscillators is configured by, for example, forming electrodes on both ends of a piezoelectric body which is a material having piezoelectricity, such as a piezoelectric ceramic typified by Lead Zirconate Titanate (PZT), polymer piezoelectric element represented by Poly Vinylidene Di Fluoride (PVDF), or a piezoelectric single crystal represented by Lead Magnesium Niobate-Lead Titanate (PMN-PT).

The transmission circuit 24 causes the oscillator array 20 to transmit an ultrasound beam toward the subject. Specifically, the transmission circuit 24 includes, for example, a plurality of pulse generators (not shown), and adjusts, based on a transmission delay pattern selected according to a control signal from an imaging control unit 30 of the body part 12, a delay amount of each of the plurality of oscillators of the oscillator array 20 and supplies the drive signal to apply a voltage. Each of the drive signals is a pulse-like or continuous wave-like voltage signal, and the piezoelectric body expands and contracts in a case in which the voltage is applied to the electrodes of the oscillators of the oscillator array 20. As a result of the above, pulse-like or continuous wave-like ultrasound is generated from each of the oscillators, and the ultrasound beam is formed from the ultrasound combination wave.

The transmitted ultrasound beam is reflected by each part (for example, a blood vessel or another tissue) in the subject, an instrument disposed in the subject, or the like to generate the ultrasound echo. The generated ultrasound echo propagates in the subject and is received by the plurality of oscillators of the oscillator array 20. Each oscillator generates the electrical signal according to the received ultrasound echo. The electrical signal generated in each oscillator is output to the reception circuit 26.

Figure 2:
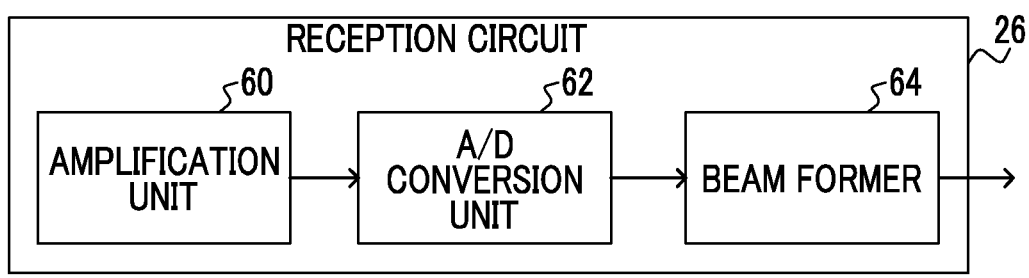
FIG. 2 is a block diagram showing an example of a configuration of a reception circuit.

The reception circuit 26 generates a sound ray signal by performing processing on a signal (strictly speaking, an analog electrical signal) output from the oscillator array 20 according to the control signal from the imaging control unit 30 of the body part 12. FIG. 2 shows a block diagram showing an example of a configuration of the reception circuit 26 according to the present embodiment. As shown in FIG. 2, the reception circuit 26 includes, for example, an amplification unit 60, an analog digital (AD) conversion unit 62, and a beam former 64.

The amplification unit 60 amplifies the electrical signal output from each of the plurality of oscillators of the oscillator array 20, and outputs the amplified electrical signal to the AD conversion unit 62. The AD conversion unit 62 converts the amplified electrical signal into digital reception data to output each of the converted reception data to the beam former 64. The beam former 64 performs reception focus processing by giving and adding the delay to each reception data converted by the AD conversion unit 62 according to a sound velocity or a sound velocity distribution set based on a reception delay pattern selected according to the control signal from the imaging control unit 30 of the body part 12. In the reception focus processing, each reception data converted by the AD conversion unit 62 is phase-adjusted and added, and the sound ray signal in which the focus of the ultrasound echo is narrowed down is generated. The generated sound ray signal is output to the image generation unit 32 of the body part 12.

On the other hand, the body part 12 comprises an imaging control unit 30, the image generation unit 32, an acquisition unit 34, a detection unit 36, a determination unit 38, and a display unit 40. As an example, the body part 12 according to the present embodiment is a portable terminal device, such as a smartphone or a tablet terminal. The body part 12 has a function of capturing the ultrasound image which is a B-mode image (tomographic image) related to the tissue in the subject from the sound ray signal obtained by scanning the subject with the ultrasound probe 10 by installing a program, such as application software. The body part 12 according to the present embodiment is an example of an information processing apparatus according to the present disclosure.

The imaging control unit 30 has a function of outputting the control signal to the transmission/reception circuit 22 of the ultrasound probe 10 as described above in a case in which the ultrasound image is captured. By inputting the control signal output from the imaging control unit 30 to the transmission circuit 24 and the reception circuit 26, the sound ray signal is output from the reception circuit 26 of the ultrasound probe 10 to the image generation unit 32, as described above.

Figure 3:
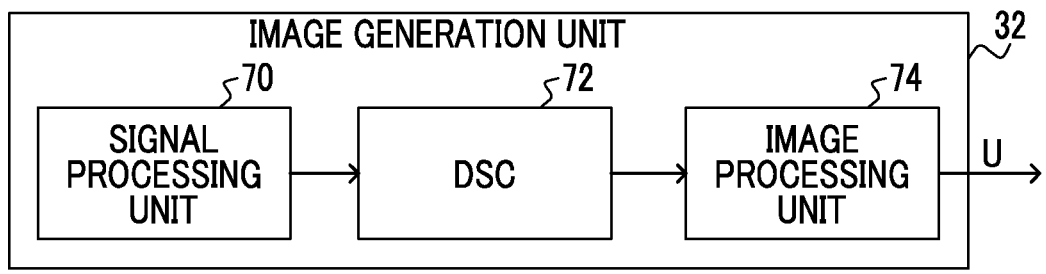
FIG. 3 is a block diagram showing an example of a configuration of an image generation unit.

The image generation unit 32 has a function of generating the ultrasound image based on the sound ray signal input from the reception circuit 26 of the ultrasound probe 10. FIG. 3 shows a block diagram showing an example of a configuration of the image generation unit 32 according to the present embodiment. As shown in FIG. 3, the image generation unit 32 includes, for example, a signal processing unit 70, a digital scan converter (DSC) 72, and an image processing unit 74. The signal processing unit 70 corrects the attenuation by the distance according to the depth of the reflection position of the ultrasound for the sound ray signal generated by the reception circuit 26, and then performs envelope detection processing to generate a B-mode image signal indicating an ultrasound image U. The DSC 72 converts the B-mode image signal generated by the signal processing unit 70 into an image signal according to a normal television signal scanning method, by raster conversion or the like. The image processing unit 74 performs various necessary image processing, such as gradation processing, on the B-mode image signal input from the DSC 72, and then outputs the B-mode image signal. The B-mode image signal output from the image generation unit 32 corresponds to the ultrasound image U.

Under the control of the imaging control unit 30, the transmission/reception circuit 22 of the ultrasound probe 10 and the image generation unit 32 of the body part 12 continuously acquire the ultrasound images at a certain frame rate a plurality of times during an imaging period of the ultrasound image.

Figure 4A:
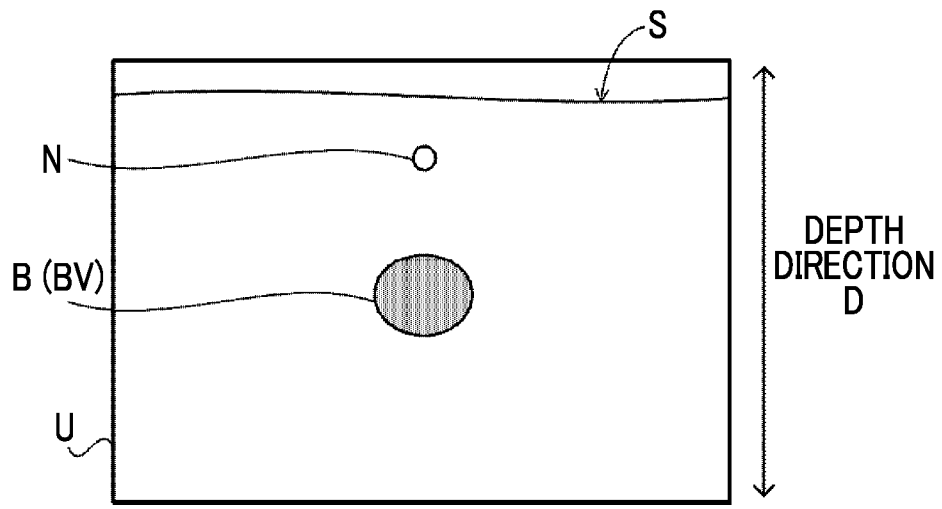
FIG. 4A is a diagram showing an example of an ultrasound image captured by a minor axis method.

It should be noted that a part at which the tomography is observed is changed depending on the ultrasound image by moving the ultrasound probe 10 in a state of being in contact with the subject, and an observation direction of the blood vessel or the like in the subject can be switched by changing a direction in which the ultrasound probe 10 is brought into contact with the subject. For example, in a case in which the ultrasound probe 10 is brought into contact with the subject in a direction intersecting an extension direction of the blood vessel and an insert in a direction in which the plurality of oscillators are arranged (that is, a scanning direction) in the oscillator array 20, that is, in a case in which the minor axis method (intersection method) is adopted, transverse cross sections of the blood vessel and the insert are observed in the ultrasound image. FIG. 4A shows an example of the ultrasound image U captured by a minor axis method. The ultrasound image U shown in FIG. 4A shows a transverse cross section of a blood vessel B and a transverse cross section of a puncture needle N, which is an example of an insert. The transverse cross section of each of the blood vessel B and the puncture needle N here means a cut surface orthogonal to the extension direction of each of the blood vessel B and the puncture needle N.

Figure 4B:
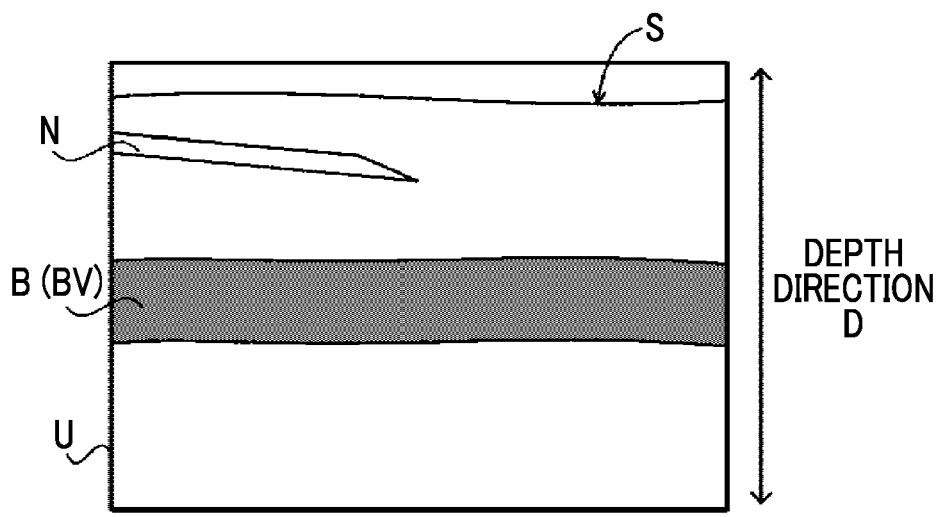
FIG. 4B is a diagram showing an example of an ultrasound image captured by a major axis method.

On the other hand, in a case in which the ultrasound probe 10 is brought into contact with the subject in a direction in which an arrangement direction (scanning direction) of the oscillators in the oscillator array 20 is along the extension direction of the blood vessel and the insert, that is, in a case in which a major axis method (paralleling method) is adopted, longitudinal cross sections of the blood vessel and the insert are observed in the ultrasound image. FIG. 4B shows an example of the ultrasound image U captured by a major axis method. The ultrasound image U shown in FIG. 4B shows a longitudinal cross section of the blood vessel B and a longitudinal cross section of the puncture needle N, which is the example of the insert. The longitudinal cross section of each of the blood vessel B and the puncture needle N here means a cut surface along the extension direction of each of the blood vessel B and the puncture needle N.

It should be noted that, in the present embodiment, as shown in FIGS. 4A and 4B, a direction connecting a body surface S and an inside of the subject in the ultrasound image U is referred to as a depth direction D. The depth direction D corresponds to a direction in which a plurality of scanning lines extend in the ultrasound image U. Each portion of the ultrasound image U, such as the blood vessel B or the puncture needle N, is displayed at the position according to the distance from the body surface of the subject with which the ultrasound probe 10 is brought into contact in the depth direction D, that is, the depth.

The ultrasound image U generated by the image generation unit 32 is output to the acquisition unit 34.

The acquisition unit 34 has a function of acquiring the ultrasound image U generated and output by the image generation unit 32. Specifically, the acquisition unit 34 has a function of imaging a predetermined region from the center to the terminal of the subject with the ultrasound probe 10 to acquire the ultrasound image U generated and output by the image generation unit 32.

In addition, the acquisition unit 34 according to the present embodiment has a function of acquiring information indicating a position of the ultrasound probe 10. As an example for detecting the position of the ultrasound probe 10, the present embodiment comprises a transmitter 14 and a magnetic sensor 16 as a three-dimensional position detection sensor. Each of the transmitter 14 and the magnetic sensor 16 includes orthogonal coils in three directions corresponding to each of an x-axis, a y-axis, and a z-axis. A three-dimensional position of the ultrasound probe 10 can be measured by sequentially exciting each coil of the transmitter 14 and measuring the electromotive force of each coil included in the magnetic sensor 16. As an example, the transmitter 14 according to the present embodiment is fixed at a predetermined position on a head side of the subject on a bed on which the subject lies in a case in which the puncture is performed. On the other hand, the magnetic sensor 16 is attached to the ultrasound probe 10.

The acquisition unit 34 outputs a detection instruction signal to the transmitter 14. In a case in which the detection instruction signal is input from the acquisition unit 34, the transmitter 14 sequentially excites the orthogonal coils in the three directions, as described above. The information indicating the position of the ultrasound probe 10 is output from the magnetic sensor 16 to the acquisition unit 34 as a detection result. In this way, the acquisition unit 34 acquires the position of the ultrasound probe 10 in a case in which the ultrasound image U is captured. The acquisition unit 34 outputs the ultrasound image U acquired from the image generation unit 32 and the information indicating the position of the ultrasound probe 10 in a case in which the ultrasound image U acquired from the magnetic sensor 16 is captured, to the detection unit 36 in association with each other.

It should be noted that, in a case in which the image generation unit 32 functions as the information processing apparatus according to the present disclosure as in the present embodiment, the functions of the image generation unit 32 and the acquisition unit 34 may be integrated. In other words, in a case in which the information processing apparatus according to the present disclosure comprises the image generation unit 32, the image generation unit 32 may further function as the acquisition unit 34.

The detection unit 36 has a function of detecting an abnormal portion at which an abnormality occurs in the blood vessel B that is a target for the puncture from the ultrasound image U input from the acquisition unit 34. It should be noted that, in the present embodiment, since the vein BV is the target for the puncture, the abnormal portion at which the abnormality occurs in the vein BV is detected. Therefore, as an example, first, the detection unit 36 according to the present embodiment detects the vein BV from the ultrasound image U. It should be noted that the method in which the detection unit 36 detects the vein BV from the ultrasound image U is not particularly limited. For example, a form may be adopted in which all the blood vessels B including the artery and the vein BV included in the ultrasound image U are detected, and the vein BV is further detected from the detected blood vessels B. In addition, for example, a form may be adopted in which only the vein BV in the blood vessels B is detected from the ultrasound image U.

As an example, the detection unit 36 according to the present embodiment analyzes the ultrasound image U acquired by the acquisition unit 34, in other words, the ultrasound image U generated by the image generation unit 32, according to a known algorithm, to detect the vein BV in the ultrasound image U. For example, the detection unit 36 can store typical pattern data of a blood vessel region in which the vein BV is present as a template in advance, derive a degree of similarity with respect to the pattern data while searching the ultrasound image U with the template, and consider that the vein BV is present in a place in which the degree of similarity is equal to or larger than a reference value and is maximized.

Also, in addition to simple template matching, the derivation of the degree of similarity includes a method using a trained learning model based on a feature amount of an image showing the vein By. For example, a machine learning method, such as Support Vector Machine (SVM) or Adaptive Boosting (AdaBoost) described in Csurka et al.: Visual Categorization with Bags of Keypoints, Proc. of ECCV Workshop on Statistical Learning in Computer Vision, pp. 59-74 (2004), or a general image recognition method using deep learning described in Krizhevsk et al.: ImageNet Classification with Deep Convolutional Neural Networks, Advances in Neural Information Processing Systems 25, pp. 1106-1114 (2012) can be used.

In addition, for example, the detection unit 36 may detect the vein BV in the ultrasound image U using a vein detection model which is a trained model that has been subjected to machine learning using a plurality of ultrasound images U labeled with respect to the vein BV. For example, the vein detection model is an object detection algorithm using deep learning. As the vein detection model, for example, an object detection model configured by a regional convolutional neural network (R-CNN), which is a type of a CNN, can be used. The vein detection model detects the vein BV as an object from the input ultrasound image U, and outputs information indicating the vein BV in the ultrasound image U.

It should be noted that the detection unit 36 according to the present embodiment detects all the veins BV included in the ultrasound image U. In a case in which a plurality of veins BV are included in the ultrasound image U, a form may be adopted in which the detection is performed for each of the plurality of veins BV by applying, for example, the template matching, the general image recognition method, or the vein detection model. In addition, for example, a form may be adopted in which one or more veins BV are collectively detected by applying the template matching, the general image recognition method, or the vein detection model.

Further, the detection unit 36 detects the abnormal portion at which the abnormality occurs in the detected vein B V. Examples of the abnormality in the vein B V include a thrombus, a portion connected to the artery for a shunt, and the like. As a specific example, in the present embodiment, a case will be described in which the abnormality is the thrombus and the abnormal portion is a portion at which the thrombus occurs in the vein By.

It should be noted that the method in which the detection unit 36 detects the abnormal portion at which the thrombus occurs in the vein BV is not particularly limited. For example, a form may be adopted in which a blood vessel diameter of the vein BV is detected in each of the plurality of ultrasound images U captured along the vein BV, and a portion at which a stenosis in which the blood vessel diameter is narrower than the blood vessel diameter in another ultrasound image U is caused is detected as the abnormal portion at which the thrombus occurs.

In addition, for example, it is possible to store typical pattern data of the thrombus in the vein BV as a template in advance, derive a degree of similarity with respect to the pattern data while searching the region of the vein BV in the ultrasound image U with the template, and consider that the thrombus is present in a place in which the degree of similarity is equal to or larger than a reference value and is maximized.

Also, in addition to simple template matching, the derivation of the degree of similarity includes a method using a trained learning model based on a feature amount of an image showing the thrombus. For example, a machine learning method such as SVM or AdaBoost described above, or a general image recognition method using deep learning described above can be used.

In addition, for example, the detection unit 36 may detect the thrombus in the vein BV in the ultrasound image U using a thrombus detection model which is a trained model that has been subjected to machine learning using a plurality of ultrasound images U labeled with respect to the thrombus. For example, the thrombus detection model is an object detection algorithm using deep learning. As the thrombus detection model, for example, an object detection model configured by a regional convolutional neural network (R-CNN), which is a type of a CNN, can be used. The thrombus detection model detects the thrombus as an object from the input ultrasound image U, and outputs information indicating the thrombus in the ultrasound image U.

It should be noted that the present invention is not limited to the present embodiment, and a form may be adopted in which the detection unit 36 directly detects the abnormal portion at which the thrombus occurs in the vein BV from the ultrasound image U.

A detection result of the detection unit 36 is output to the determination unit 38. Specifically, the information indicating the vein BV in the ultrasound image U detected by the detection unit 36 and the information on the abnormal portion at which the thrombus occurs in the vein BV are output to the determination unit 38. It should be noted that, in the present embodiment, the position of the ultrasound probe 10 associated with the ultrasound image U is adopted as the abnormal portion.

Figure 5:
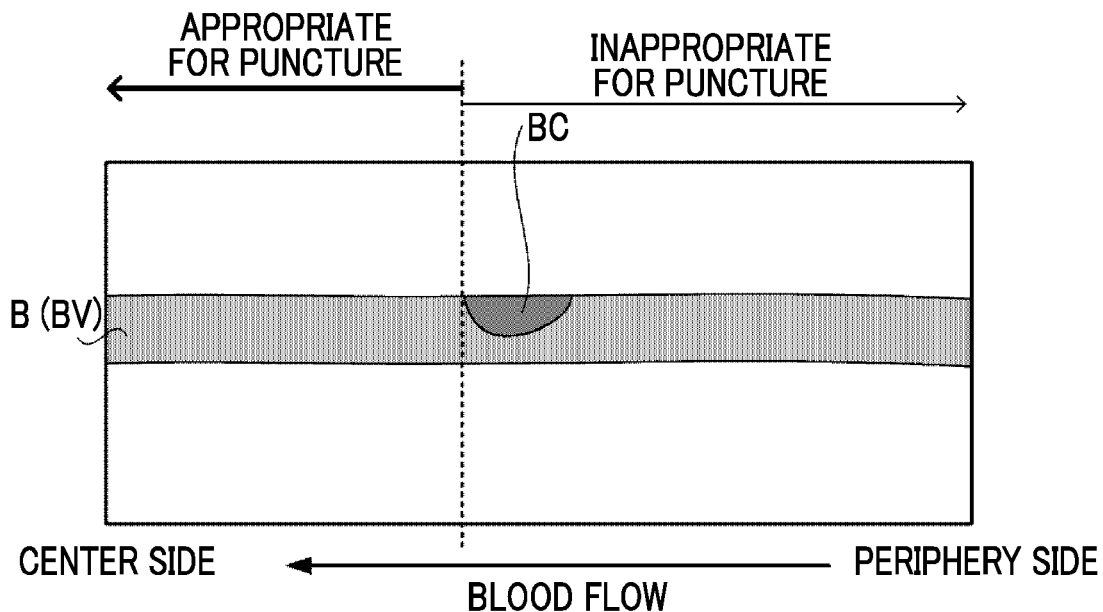
FIG. 5 is a diagram for describing whether a puncture for an abnormal portion is appropriate or inappropriate.

The determination unit 38 has a function of determining whether the puncture in the vein BV is appropriate or inappropriate and outputting the determination result according to the abnormal portion detected by the detection unit 36. It may not be preferable to perform the puncture on the periphery side with respect to the abnormal portion at which the abnormality occurs in the vein By. In particular, in a case in which blood, an infusion solution, or the like is allowed to flow into the vein BV by the puncture, it may not be preferable to perform the puncture on the periphery side with respect to the abnormal portion, and thus the description will be made with reference to FIG. 5. It should be noted that, in the present embodiment, a "center side" refers to a side close to the heart of the subject, and the "periphery side" refers to a terminal side, such as a fingertip of the subject. As shown in FIG. 5, in the vein BV, the blood flows from the periphery side to the center side. In other words, the blood flow in the vein BV is in a direction from the periphery side toward the center side. In a case in which a thrombus BC occurs in the vein BV, in a case in which the puncture is performed on the periphery side with respect to the thrombus BC and the blood or the infusion solution is allowed to flow, there is a risk that the thrombus BC is exfoliated by inflowing blood or infusion solution and the exfoliated thrombus BC reaches the circulatory organ. Therefore, in the present embodiment, as shown in FIG. 5, it is inappropriate to perform the puncture on the periphery side with respect to the abnormal portion at which the thrombus BC occurs in the vein BV. In other words, it is appropriate to perform the puncture on the center side with respect to the abnormal portion at which the thrombus BC occurs in the vein By.

Therefore, the detection unit 36 according to the present embodiment determines that it is inappropriate to perform the puncture in the vein BV on the periphery side with respect to the abnormal portion at which the thrombus BC occurs in the vein BV, and determines that it is appropriate to perform the puncture in the vein BV on the center side with respect to the abnormal portion.

The determination unit 38 outputs information indicating a warning in a case of determining that it is inappropriate to perform the puncture. As an example, in the present embodiment, the ultrasound image U input from the acquisition unit 34 is added as the information indicating that it is inappropriate to perform the puncture as the information indicating the warning and output to the display unit 40. On the other hand, in a case in which the determination unit 38 determines that it is appropriate to perform the puncture, only the ultrasound image U input from the acquisition unit 34 is output to the display unit 40.

The display unit 40 has a function of displaying various types of information, such as an ultrasound image U or the ultrasound image U to which the information indicating the warning output from the display unit 40 is added. Examples of the display unit 40 include a liquid crystal display (LCD), an organic electro luminescence (EL) display, and a head mounted display.

Figure 6:
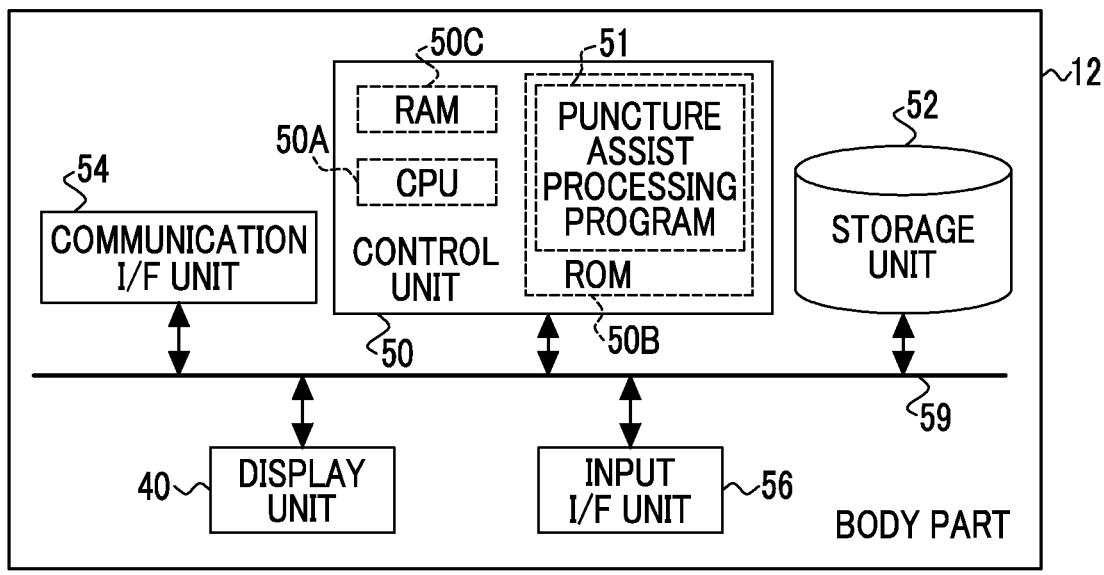
FIG. 6 is a configuration diagram showing an example of a hardware configuration of a body part according to the embodiment.

The body part 12 can be configured by, for example, the hardware shown in FIG. 6. FIG. 6 shows a configuration diagram showing an example of a hardware configuration of the body part 12 according to the present embodiment. As shown in FIG. 6, the body part 12 comprises the display unit 40, a control unit 50, the storage unit 52, a communication interface (I/F) unit 54, and the input I/F unit 56. The display unit 40, the control unit 50, the storage unit 52, the communication I/F unit 54, and the input I/F unit 56 are connected to each other through a bus 59, such as a system bus or a control bus, such that various types of information can be exchanged.

The control unit 50 controls an overall operation of the body part 12. The control unit 50 comprises a central processing unit (CPU) 50A, a read only memory (ROM) 50B, and a random access memory (RAM) 50C. The ROM 50B stores, in advance, various programs and the like, which are executed by the CPU 50A and include a puncture assist processing program 51 and an imaging program (not shown). The RAM 50C transitorily stores various data. The puncture assist processing program 51 according to the present embodiment is an example of an information processing program according to the present disclosure.

The CPU 50A executes the imaging program stored in the ROM 50B, so that the CPU 50A functions as the imaging control unit 30. In addition, the CPU 50A executes the puncture assist processing program 51 stored in the ROM 50B, so that the CPU 50A functions as the acquisition unit 34, the detection unit 36, and the determination unit 38.

The storage unit 52 stores image data of the ultrasound image U generated by the image generation unit 32, the information indicating the position of the ultrasound probe 10, various other information, and the like. Specific examples of the storage unit 52 include a hard disk drive (HDD), a solid state drive (SSD), and a secure digital (SD) card.

The input I/F unit 56 is used for the user to input instructions and various types of information related to capturing of the ultrasound image U and the like. The input I/F unit 56 is not particularly limited, and examples thereof include various switches, a touch panel, a touch pen, a camera, and a mouse. It should be noted that the display unit 40 and the input I/F unit 56 may be integrated to form a touch panel display.

The communication I/F unit 54 performs communication of various types of information with the ultrasound probe 10, the transmitter 14, the magnetic sensor 16, and an external device of the ultrasound diagnostic apparatus 1 by wireless communication, such as WiFi (registered trademark) or Bluetooth (registered trademark) or wired communication. As described above, the body part 12 outputs the control signal for capturing the ultrasound image U to the ultrasound probe 10 through the communication I/F unit 54. In addition, the sound ray signal is input from the ultrasound probe 10 to the body part 12 through the communication OF unit 54. In addition, the detection instruction signal for detecting the position of the ultrasound probe 10 is output from the body part 12 to the transmitter 14 through the communication OF unit 54. In addition, the information indicating the position of the ultrasound probe 10 is input from the magnetic sensor 16 to the body part 12 through the communication I/F unit 54.

Next, an action of the body part 12 according to the present embodiment will be described with reference to the drawings.

Figure 7:
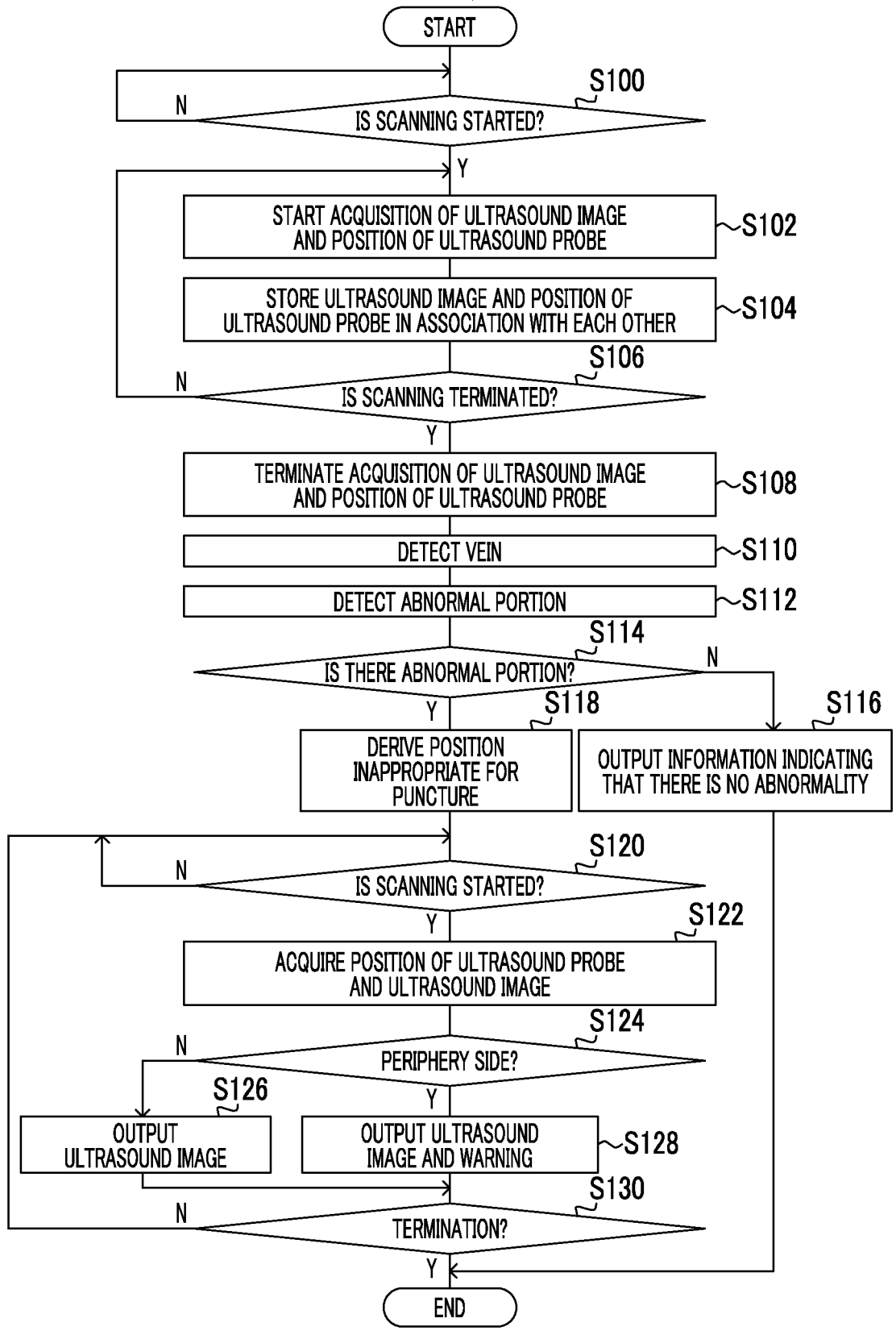
FIG. 7 is a flowchart showing an example of a flow of puncture assist processing by the body part according to the embodiment.

As an example, in the body part 12 according to the present embodiment, the CPU 50A of the control unit 50 executes the puncture assist processing program 51 stored in the ROM 50B to execute puncture assist processing shown in FIG. 7. FIG. 7 shows a flowchart showing an example of a flow of the puncture assist processing executed in the body part 12 according to the present embodiment. The puncture assist processing shown in FIG. 7 is executed, for example, in a case in which a power of the body part 12 is turned on or a case in which the execution is instructed by the user through the input I/F unit 56.

In a case in which the puncture is performed, in order to search for the portion at which the puncture is performed, the user scans a body surface of the subject by the ultrasound probe 10 from the center side to the periphery side with respect to the part of the subject in which the puncture is performed, such as the upper limb or the lower limb, or from the periphery side to the center side. It should be noted that the region in which the body surface of the subject is scanned by the ultrasound probe 10 in the present embodiment is an example of a predetermined region according to the present disclosure. It should be noted that, hereinafter, as an example, a form will be described in which the scanning from the center side to the periphery side of the subject is predetermined.

In step S100 of FIG. 7, the acquisition unit 34 determines whether or not the scanning of the subject by the ultrasound probe 10 is started. The method in which the acquisition unit 34 determines whether or not the scanning of the subject is started is not particularly limited. For example, a form may be adopted in which the acquisition unit 34 determines that the scanning is started by acquiring scanning start information input by the user through the input I/F unit 56. In addition, for example, a form may be adopted in which the acquisition unit 34 determines that the scanning is started in a case in which the ultrasound probe 10 is changed from an aerial radiation state to a state of contacting with the subject by using image recognition or a temperature sensor. It should be noted that the aerial radiation state refers to a state in which the ultrasound probe 10 is separated from the body surface of the subject and radiates the ultrasound in the air. As technology of detecting whether the ultrasound probe 10 is in the aerial radiation state or the state of contacting with the subject, for example, technology disclosed in WO2017/033502A can be applied. The technology disclosed in WO2017/033502A is the technology resulting from the fact that any structure in the ultrasound image U, that is, the tissue in the subject is drawn in a case in which the ultrasound probe 10 is brought into contact with the body surface of the subject and radiates the ultrasound into the body of the subject, but the structure in the ultrasound image U is not drawn in a case in which the ultrasound probe 10 is separated from the body surface of the subject and radiates the ultrasound in air. That is, the presence or absence of the structure in the ultrasound image U generated by the image generation unit 32 is detected, and it is determined that the ultrasound probe 10 is in the state of contacting with the subject in a case in which the presence of the structure in the ultrasound image U is detected. On the other hand, in a case in which it is detected that there is no structure in the ultrasound image U, it is determined that the ultrasound probe 10 is in the aerial radiation state.

A negative determination is made in the determination in step S100 until the scanning of the subject by the ultrasound probe 10 is started. On the other hand, in a case in which the scanning of the subject by the ultrasound probe 10 is started, an affirmative determination is made in the determination in step S100, and the processing proceeds to step S102.

In step S102, the acquisition unit 34 starts the acquisition of the ultrasound image U and the position of the ultrasound probe 10. As described above, the acquisition unit 34 according to the present embodiment acquires the ultrasound image U from the image generation unit 32, and acquires the information indicating the position of the ultrasound probe 10 in a case in which the acquired ultrasound image U is captured, from the magnetic sensor 16. The acquisition unit 34 outputs the ultrasound image U and the information indicating the position of the ultrasound probe 10 in a case in which the ultrasound image U is captured, to the detection unit 36 in association with each other.

In next step S104, the detection unit 36 stores the acquired ultrasound image U in the storage unit 52 in a state in which the ultrasound probe 10 is associated with the acquired ultrasound image U.

In next step S106, the acquisition unit 34 determines whether or not the scanning of the subject by the ultrasound probe 10 is terminated. The method in which the acquisition unit 34 determines whether or not the scanning of the subject is terminated is not particularly limited. For example, a form may be adopted in which the acquisition unit 34 determines that the scanning is terminated by acquiring scanning termination information input by the user through the input I/F unit 56. In addition, for example, a form may be adopted in which the acquisition unit 34 determines that the scanning is terminated in a case in which the ultrasound probe 10 is changed from the state of contacting with the subject to the aerial radiation state. It should be noted that, as technology for detecting whether the ultrasound probe 10 in this case is in the aerial radiation state or the state of contacting with a subject, the technology described in step S100 can be applied.

In a case in which the scanning of the subject by the ultrasound probe 10 is not terminated, a negative determination is made in the determination in step S106, the processing returns to step S102, the processing of steps S102 and S104 is repeated, and the acquisition and the storage of the ultrasound image U and the position of the ultrasound probe 10 are repeated. On the other hand, in a case in which the scanning of the subject by the ultrasound probe 10 is terminated, an affirmative determination is made in the determination in step S106, and the processing proceeds to step S108.

In step S108, the acquisition unit 34 terminates the acquisition of the ultrasound image U and the position of the ultrasound probe 10.

In next step S110, the detection unit 36 detects the vein BV from the ultrasound image U, as described above.

In next step S112, the detection unit 36 detects the abnormal portion at which the thrombus BC occurs from the vein BV in the ultrasound image U, as described above. Specifically, the position of the ultrasound probe 10 in the case in which the ultrasound image U in which the thrombus BC occurs in the vein BV is captured is detected. It should be noted that, in a case in which the plurality of veins BV are detected in step S110, the thrombus BC in each vein BV is detected. In addition, in a case in which a plurality of thrombi BC are detected for one vein BV, the abnormal portion at which each thrombus BC occurs is detected for all the thrombi BC. The detection unit 36 outputs the information indicating the abnormal portion at which the detected thrombus BC occurs to the determination unit 38.

In next step S114, the determination unit 38 determines whether or not there is the abnormal portion. In a case in which the abnormal portion is detected in step S112, specifically, in a case in which the information indicating that there is no abnormal portion is input from the detection unit 36 to the determination unit 38, since the thrombus BC does not occur in all the veins BV in a scanning range, a negative determination is made in the determination in step S114, and the processing proceeds to step S116.

Figure 8:
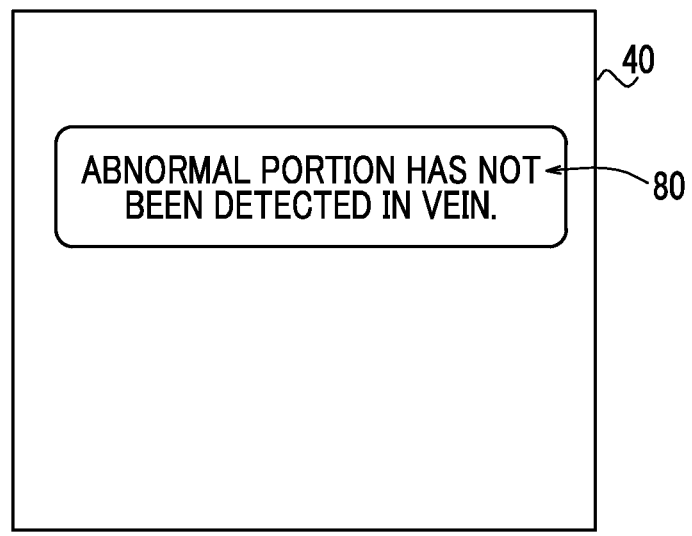
FIG. 8 is a diagram showing an example of a state in which information indicating that there is no abnormal portion is displayed on a display unit.

In step S116, the determination unit 38 outputs the information indicating that there is no abnormal portion at which the thrombus BC occurs in all the veins BV in the scanning range to the display unit 40. As a result, as in the example shown in FIG. 8, information 80 indicating that there is no abnormal portion is displayed on the display unit 40. In a case in which the information 80 indicating that there is no abnormal portion is displayed on the display unit 40, the user performs the puncture at a desired portion in the scanning range. It should be noted that, in this case, so-called echo-guided puncture may be performed by scanning the subject again by the ultrasound probe 10 to capture the ultrasound image U and referring to the ultrasound image U acquired by the image generation unit 32 and displayed on the display unit 40. In addition, the puncture may be performed without scanning the subject, in other words, without capturing the ultrasound image U. In a case in which the processing of step S116 is terminated, the puncture assist processing shown in FIG. 7 is terminated.

On the other hand, in a case in which the abnormal portion is detected in step S112, an affirmative determination is made in the determination in step S114, and the processing proceeds to step S118. In step S118, the determination unit 38 derives a position inappropriate for the puncture. As shown in FIG. 5, the determination unit 38 derives, for each of the detected veins BV, the periphery side with respect to the abnormal portion at which the thrombus BC occurs as the position inappropriate for the puncture. In other words, the determination unit 38 derives, for each detected vein BV, the center side with respect to the abnormal portion at which the thrombus BC occurs as a position appropriate for the puncture. It should be noted that, in a case in which the plurality of thrombi BC are generated in one vein BV, as described above, from the viewpoint of suppressing the exfoliation of the thrombi BC, the position on the periphery side with respect to the abnormal portion at which the thrombus BC on the most center side occurs is derived as the position inappropriate for the puncture. In other words, in a case in which the plurality of thrombi BC are generated in one vein BV, the determination unit 38 derives the position on the center side with respect to the abnormal portion at which the thrombus BC on the most center side occurs as the position appropriate for the puncture.

It should be noted that, in a case in which the position at which the abnormal portion is generated is close to the center side of the subject, for example, in a case in which the position is within several cm from the most center side in a scanning region, the determination unit 38 may determine for the blood vessel B that the puncture at the part is inappropriate and derive a part on the opposite side as the position appropriate for the puncture.

As described above, in the present embodiment, in a case in which the vein BV has the abnormal portion, the information 80 indicating that there is no abnormal portion is not displayed on the display unit 40. As a result, the user can recognize that the abnormal portion is present in the vein BV within the scanning range. In this case, the user scans the scanning range again in order to search for the position at which the puncture is performed.

Therefore, in next step S120, the acquisition unit 34 determines whether or not the scanning of the subject by the ultrasound probe 10 is started in the same manner as in step S100. A negative determination is made in the determination in step S120 until the scanning of the subject is started. On the other hand, in a case in which the scanning of the subject is started, an affirmative determination is made in the determination in step S120, and the processing proceeds to step S122.

In step S122, the acquisition unit 34 acquires the ultrasound image U and the position of the ultrasound probe 10. The acquisition unit 34 outputs the ultrasound image U and the information indicating the position of the ultrasound probe 10 in a case in which the ultrasound image U is captured, to the determination unit 38 in association with each other.

In next step S124, the determination unit 38 determines whether or not the position of the ultrasound probe 10 acquired in step S122 is positioned on the periphery side with respect to the abnormal portion at which the thrombus BC detected in step S112 occurs. The determination unit 38 according to the present embodiment determines whether or not the position is positioned on the periphery side with respect to the abnormal portion by determining whether or not the position of the ultrasound probe 10 is included in the position inappropriate for the puncture derived in step S118. In a case in which the position of the ultrasound probe 10 is not positioned on the periphery side with respect to the abnormal portion at which the thrombus BC occurs, in other words, in a case in which the position is positioned on the center side with respect to the abnormal portion at which the thrombus BC occurs, a negative determination is made in the determination in step S124, and the processing proceeds to step S126.

Figure 9A:
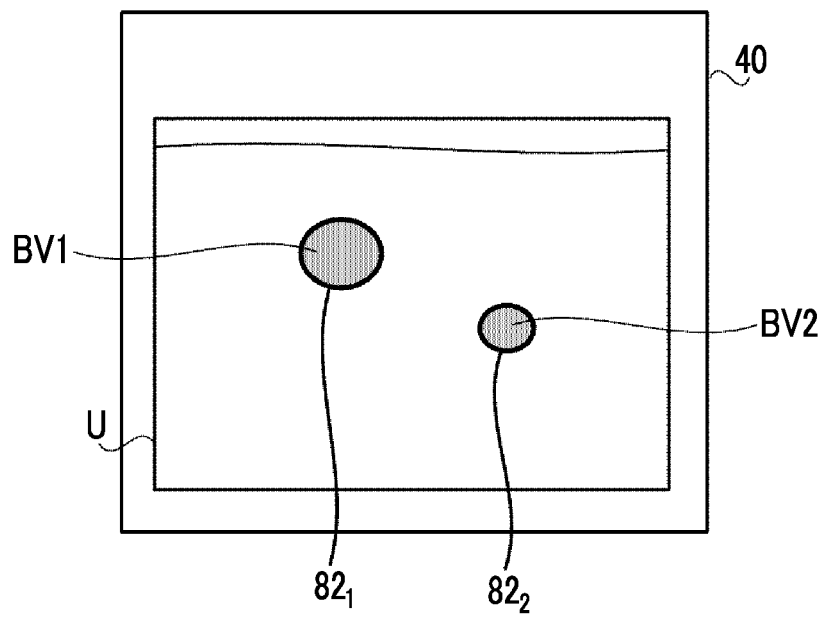
FIG. 9A is a diagram showing an example of a state in which an ultrasound image captured at a position appropriate for the puncture is displayed on the display unit.

In step S126, the determination unit 38 outputs the ultrasound image U acquired in step S122 to the display unit 40, and then the processing proceeds to step S130. FIG. 9A shows an example of the ultrasound image U displayed on the display unit 40 in this case. In the example shown in FIG. 9A, an example of a state is shown in which the ultrasound image U including two veins BV of a vein BV1 and a vein BV2 is displayed on the display unit 40. In addition, in the example shown in FIG. 9A, a form example is shown in which information 821 and 822 indicating the respective positions are added to the vein BV1 and the vein BV2, respectively, and displayed. It should be noted that, in the example shown in FIG. 9A, a form example is shown in which a relatively thick solid line enclosing an outer shape of each of the veins BV1 and BV2 is applied as the information 821 and 822. As described above, the determination unit 38 according to the present embodiment adds the information indicating the position of the vein BV to the ultrasound image U and outputs the information to the display unit 40. The position of the vein BV can be guided to the user by emphasizing the vein BV in the ultrasound image U in this way. It should be noted that the information indicating the position of the vein BV is not limited to the form shown as the information 821 and 822. For example, a form may be adopted in which the outer shape of the vein BV is enclosed by a solid line having a relatively conspicuous color.

By displaying the ultrasound image U as shown in FIG. 9A, the user can recognize that the current position of the ultrasound probe 10 is the position appropriate for the puncture of the vein BV displayed on the display unit 40.

In this way, the determination unit 38 can guide the position of the vein BV to the user by emphasizing the vein BV detected in step S110 in the ultrasound image U output to the display unit 40.

Figure 9B:
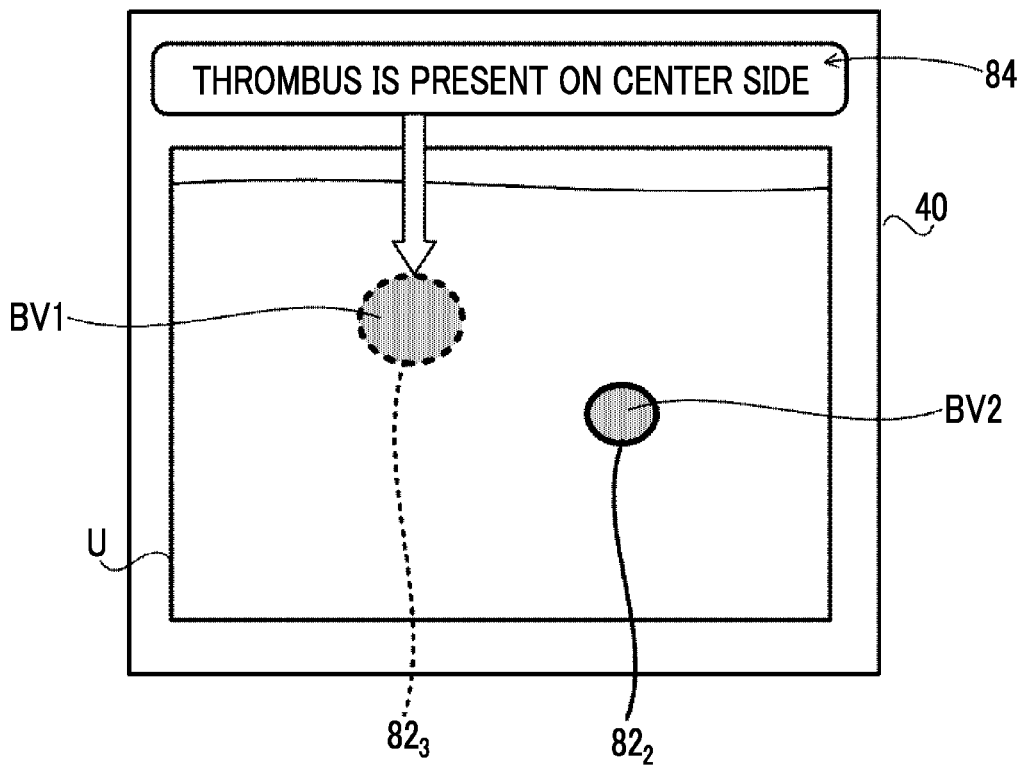
FIG. 9B is a diagram showing an example of a state in which an ultrasound image captured at a position inappropriate for the puncture and information indicating a warning are displayed on the display unit.

On the other hand, in step S124, in a case in which the position of the ultrasound probe 10 is positioned on the periphery side with respect to the abnormal portion at which the thrombus BC occurs, an affirmative determination is made in the determination, and the processing proceeds to step S128. In step S128, the determination unit 38 adds the information indicating the warning to the ultrasound image U acquired in step S122 and outputs the information to the display unit 40, and then the processing proceeds to step S130. FIG. 9B shows an example of the ultrasound image U and information 84 representing the warning which are displayed on the display unit 40 in this case. In the example shown in FIG. 9B, an example of a state is shown in which the ultrasound image U including two veins BV of the vein BV1 and the vein BV2, and the information 84 indicating the warning for the vein BV1 are displayed on the display unit 40. It should be noted that, as shown in FIG. 9B, in the present embodiment, in a case in which the plurality of veins BV are present, the information 84 indicating the warning is displayed so that it can be recognized whether or not there is the thrombus on the center side for any vein BV among the plurality of veins By.

In addition, in the example shown in FIG. 9B, a form example is shown in which information 823 and 822 indicating the respective positions are added to the vein BV1 and the vein BV2, respectively, and displayed. As shown in FIG. 9B, whether the puncture is appropriate or inappropriate can be more clearly displayed by making the display forms of the information 823 and 822 indicating the respective positions different between the vein BV1 in which the puncture is inappropriate and the vein BV2 in which the puncture is appropriate. The method of making the display forms different is not particularly limited, and for example, as shown in FIG. 9B, a form may be adopted in which the types of line, such as a solid line or a dotted line, are made different. In addition, for example, a form may be adopted in which the colors of the lines are made different.

By displaying the information 84 indicating the warning as shown in FIG. 9B, the user can recognize that the position is inappropriate for the puncture of the vein BV1. In this case, the user performs the puncture at a position on the center side with respect to the current position of the ultrasound probe 10.

In step S130, the determination unit 38 determines whether or not the puncture is terminated. In the present embodiment, it is determined that the puncture is terminated in a case in which a predetermined termination condition is satisfied, such as a case in which the user instructs the termination of the puncture through the input I/F unit 56, a case in which the power of the body part 12 is cut off, or a case in which the ultrasound probe 10 is changed from the state of contacting with the subject to the aerial radiation state. In a case in which the termination condition is not satisfied, a negative determination is made in the determination in step S130, the processing returns to step S120, and the processing of steps S120 to S130 is repeated. On the other hand, in a case in which the termination condition is satisfied in step S130, an affirmative determination is made, and the puncture assist processing shown in FIG. 7 is terminated.

It should be noted that, in the form described above, the form has been described in which the transmitter 14 is fixed at a predetermined position on the head side of the subject on the bed on which the subject lies, but the position at which the transmitter 14 is provided is not limited to the present form. For example, a form may be adopted in which the transmitter 14 is directly fixed at a predetermined part, such as a wrist or an ankle of the subject.

In addition, the detection of the position of the ultrasound probe 10 does not have to derive the three-dimensional position as described above, and the detection method is not particularly limited as long as it is possible to identify the position of the ultrasound probe 10 within the scanning region from the center side to the periphery side of the subject, more specifically, to identify whether the position is positioned on the center side or periphery side with respect to the abnormal portion. For example, in a case in which the transmitter 14 is fixed at a predetermined position on the head side of the subject on the bed on which the subject lies as in the form described above, a distance between the transmitter 14 and the magnetic sensor 16 is long, it is possible to detect that the ultrasound probe 10 is positioned on the periphery side. Also, in a case in which the distance between the transmitter 14 and the magnetic sensor 16 is short, it is possible to detect that the ultrasound probe 10 is positioned on the center side.

It should be noted that the present invention is not limited to the present form. The modification examples 1 and 2 will be shown as a modification example of the method of acquiring the position of the ultrasound probe 10.

Modification Example 1

In the present modification example, as the modification example of the method of acquiring the position of the ultrasound probe 10, a modification example of a form using an imaging apparatus that captures a distance image will be described.

Figure 10:
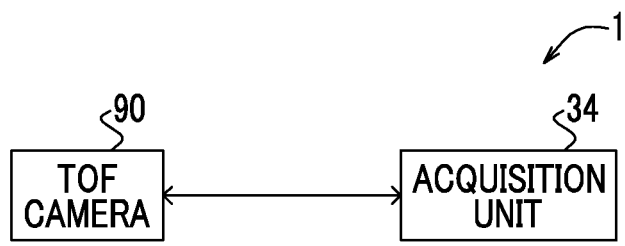
FIG. 10 is a block diagram showing an example of a partial configuration of an ultrasound diagnostic apparatus according to a modification example 1.

As shown in FIG. 10, the ultrasound diagnostic apparatus 1 according to the present embodiment comprises a TOF camera 90 instead of the transmitter 14 and the magnetic sensor 16 of the ultrasound diagnostic apparatus 1 (see FIG. 1) according to the form described above. It should be noted that, since other configurations are the same as the configurations of the ultrasound diagnostic apparatus 1 (see FIG. 1) according to the form described above, the description in FIG. 10 is omitted.

The time of flight (TOF) camera 90 is a camera that captures the distance image showing a distance to an imaging target by using a TOF system. Specifically, the TOF camera 90 irradiates the imaging target with light, such as infrared rays, and measures a distance between the TOF camera 90 and the imaging target based on a time until the reflected light is received or a phase change between the emitted light and the received light. The distance image captured by the TOF camera 90 has distance information indicating the distance between the TOF camera 90 and the imaging target for each pixel. It should be noted that the distance image is an image from which the distance to the imaging target can be derived. The distance image captured by the TOF camera 90 has the information indicating the distance between the TOF camera 90 and the imaging target as a pixel value of each pixel.

In the present modification example, a landmark is provided, as a mark for measuring the distance, on the wrist or the ankle of the subject, or on the head side or an ankle side of the subject on the bed on which the subject lies in a case in which the puncture is performed. In addition, the TOF camera 90 is installed in the ultrasound probe 10, and the distance image showing the distance between the landmark and the TOF camera 90 is captured by the TOF camera 90. The acquisition unit 34 acquires the distance image from the TOF camera 90 through the communication I/F unit 54. The acquisition unit 34 derives the distance between the ultrasound probe 10 and the landmark from the pixel value of the acquired distance image to acquire the position of the ultrasound probe 10.

For example, in a case in which the landmark is provided on the periphery side, such as the ankle of the subject, it is possible to derive that the ultrasound probe 10 is positioned closer to the periphery side as the distance derived from the distance image is smaller. In addition, for example, in a case in which the landmark is provided on the center side, such as the head of the subject, it is possible to derive that the ultrasound probe 10 is positioned closer to the periphery side as the distance derived from the distance image is larger. It should be noted that, as described above, in the distance image, since the pixel value corresponds to the distance between the TOF camera 90 and the imaging target, a form may be adopted in which the pixel value is used instead of the distance without deriving the distance itself.

It should be noted that, contrary to the above example, a form may be adopted in which the TOF camera 90 is provided on the wrist or the ankle of the subject, or on the head side or the ankle side of the subject on the bed on which the subject lies in a case in which the puncture is performed, and the landmark is provided on the ultrasound probe 10 or the ultrasound probe 10 itself is used as the landmark.

In addition, in the present modification example, although the form example has been described in which the distance image is captured by using the TOF camera 90, a form may be adopted in which the distance image is captured by using another imaging apparatus. For example, a form may be adopted in which the distance image is captured by applying a structured light method using a distance image capturing apparatus that irradiates the imaging target with infrared rays having a pattern to capture the distance image according to reflected light from the imaging target. In addition, for example, a form may be adopted in which a depth from defocus (DFD) method of restoring the distance based on a status of blurriness of an edge region reflected in the distance image is applied. In the case of this form, for example, a form is known in which a distance image captured by a monocular camera using a color aperture filter is used.

Modification Example 2

In the present modification example, as the modification example of the method of acquiring the position of the ultrasound probe 10, a modification example of a form using an optical position sensor will be described.

Figure 11:
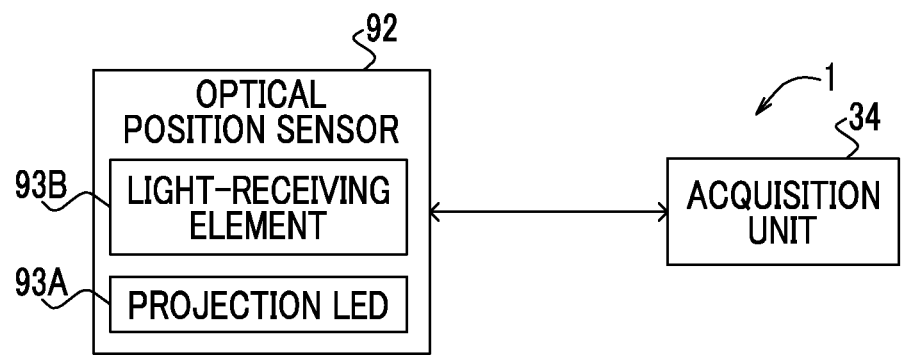
FIG. 11 is a block diagram showing an example of a partial configuration of an ultrasound diagnostic apparatus according to a modification example 2.

As shown in FIG. 11, the ultrasound diagnostic apparatus 1 according to the present embodiment comprises an optical position sensor 92 instead of the transmitter 14 and the magnetic sensor 16 of the ultrasound diagnostic apparatus 1 (see FIG. 1) according to the form described above. It should be noted that, since other configurations are the same as the configurations of the ultrasound diagnostic apparatus 1 (see FIG. 1) according to the form described above, the description in FIG. 11 is omitted.

The optical position sensor 92 is an optical sensor to which the principle of triangulation is applied, and has a function of measuring an angle of the reflected light reflected by the measurement object due to a change in the distance to the measurement object, in other words, the distance to the measurement object by using a change in the light focus position on the light-receiving element.

As shown in FIG. 11, the optical position sensor 92 includes a projection light emitting diode (LED) 93A and a light-receiving element 93B. The projection LED 93A has a function of projecting measurement light onto a measurement object, and examples thereof include a laser diode. The light-receiving element 93B has a function of receiving the reflected light generated by the measurement light projected from the projection LED 93A being reflected by the measurement object, and examples thereof include a photocoupler and the like. The optical position sensor 92 derives a distance from a light focus position on the light-receiving element 93B to the measurement object.

In the present modification example, a reflector for reflecting the measurement light projected from the optical position sensor 92 is provided on the wrist or the ankle of the subject, or on the head side or the ankle side of the subject on the bed on which the subject lies in a case in which the puncture is performed. In addition, the optical position sensor 92 is installed in the ultrasound probe 10, and the distance between the reflector and the optical position sensor 92 is measured by the optical position sensor 92. The acquisition unit 34 acquires the distance between the reflector and the optical position sensor 92 from the optical position sensor 92 through the communication I/F unit 54. The acquisition unit 34 acquires the acquired distance between the reflector and the optical position sensor 92 to acquire the position of the ultrasound probe 10.

For example, in a case in which the reflector is provided on the periphery side, such as the ankle of the subject, it is possible to derive that the ultrasound probe 10 is positioned closer to the periphery side as the distance between the reflector and the optical position sensor 92 is smaller. In addition, for example, in a case in which the landmark is provided on the center side, such as the head of the subject, it is possible to derive that the ultrasound probe 10 is positioned closer to the periphery side as the distance between the reflector and the optical position sensor 92 is larger.

It should be noted that, contrary to the above example, a form may be adopted in which the optical position sensor 92 is provided on the wrist or the ankle of the subject, or on the head side or the ankle side of the subject on the bed on which the subject lies in a case in which the puncture is performed, and the reflector is provided on the ultrasound probe 10 or the ultrasound probe 10 itself is used as the reflector.

It should be noted that the method of acquiring the position of the ultrasound probe 10 is not limited to the modification examples 1 and 2, and various other methods can also be applied. For example, a form may be adopted in which the position of the ultrasound probe 10 is acquired by using a global positioning system (GPS). In a case of the present form, for example, a form may be adopted in which a position of a base point provided on the wrist or the ankle of the subject, or on the head side or the ankle side of the subject on the bed on which the subject lies in a case in which the puncture is performed, the position of the ultrasound probe 10 are acquired by the acquisition unit 34 from the GPS through the communication I/F unit 54. In this case, for example, in a case in which the base point is provided on the periphery side of the subject, it is possible to derive that the ultrasound probe 10 is positioned closer to the periphery side as the distance derived from the position of each of the base point and the ultrasound probe 10 is smaller.

As described above, the body part 12 according to the form described above comprises the acquisition unit 34 that acquires the ultrasound image U of the vein BV in the predetermined region from the center to the periphery of the subject, the detection unit 36 that detects the abnormal portion at which the abnormality occurs in the vein BV from the acquired ultrasound image U, and the determination unit 38 that determines whether the puncture in the vein BV is appropriate or inappropriate according to the detected abnormal portion, and outputs the determination result.

Therefore, with the body part 12 according to the present form, it is possible to perform assistance of a puncture position in consideration of the abnormality in the blood vessel with respect to the user who performs the puncture of the blood vessel. In addition, with the body part 12 according to each form described above, since the user who performs the puncture can easily recognize the position appropriate for the puncture, it is easy to specify an appropriate blood vessel B for the puncture or the position of the blood vessel.

It should be noted that the technology according to the present disclosure is not limited to each form described above, and further various modifications can be made.

For example, in the puncture assist processing according to the form described above (see FIG. 7), the form has been described in which the user performs the puncture after detecting the abnormal portion from the ultrasound image U (step S114). The present invention is not limited to the present form, and the detection of the abnormal portion in the vein BV and the puncture of the vein BV may be performed at different timings. That is, a form may be adopted in which the processing of steps S100 to S118 of the puncture assist processing shown in FIG. 7 is performed in advance, the position inappropriate for the puncture or the position appropriate for the puncture is stored as puncture appropriate/inappropriate position information in the storage unit 52 or the like in association with the subject and the puncture part. In a case in which the puncture is actually performed, the puncture appropriate/inappropriate position information stored in the storage unit 52 need only be read out, and the processing after step S120 of the puncture assist processing shown in FIG. 7 need only be performed.

In addition, in the puncture assist processing according to each form described above (see FIG. 7), the form has been described in which the abnormal portion of the vein BV is detected once and the subject is scanned by the ultrasound probe 10 for the puncture again, that is the form in which the subject is scanned twice for the puncture, but the present invention is not limited to the present form, and a form may be adopted in which the detection of the abnormal portion and the puncture are performed in one scanning. In this case, for example, a form may be adopted in which, during the movement of the ultrasound probe 10 from the center side to the periphery side of the subject, the body part 12 sequentially acquires the ultrasound images U and detects the abnormal portion, and displays the information indicating the warning at the time when the abnormal portion is detected, on the display unit 40. The user who performs the puncture can recognize the region scanned before the time when the information indicating the warning is displayed on the display unit 40 as the position appropriate for the puncture.

Figure 12:
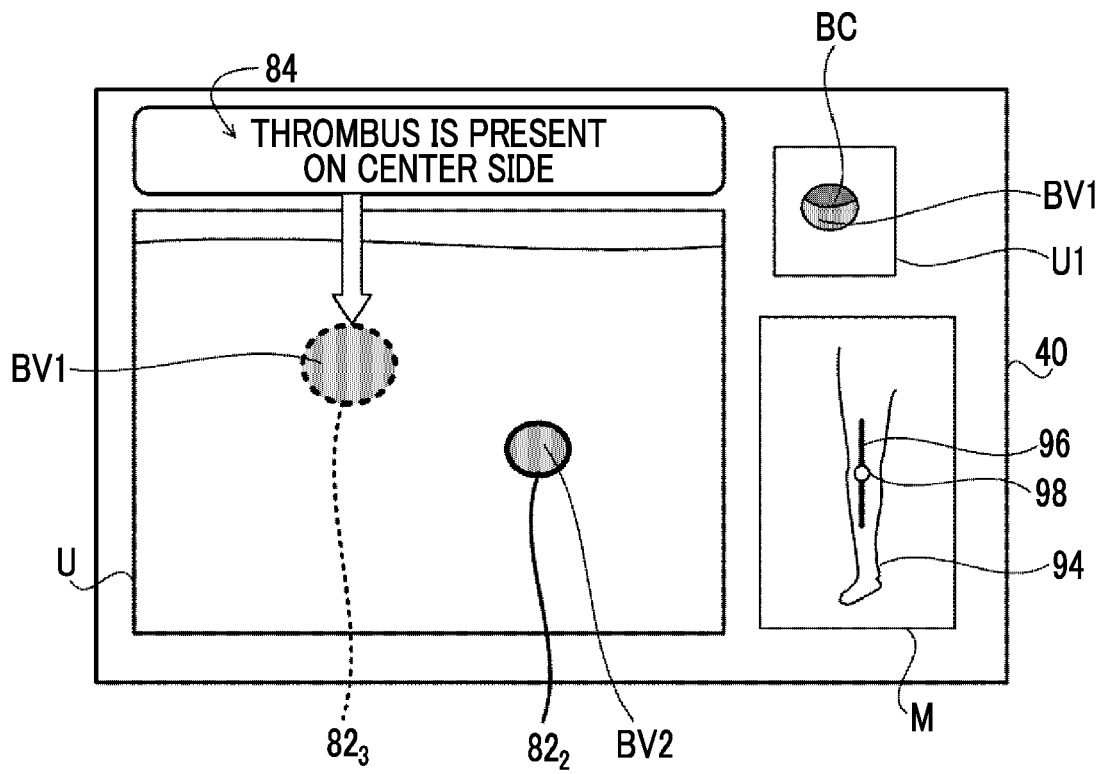
FIG. 12 is a diagram showing another example of a state in which the ultrasound image captured at the position inappropriate for the puncture and the information indicating the warning are displayed on the display unit.

In addition, a form may be adopted in which the display unit 40 displays another information for assisting the puncture on the display unit 40 in addition to the ultrasound image U and the information indicating whether the puncture is appropriate or inappropriate. In addition to the example shown in FIG. 9B, FIG. 12 shows a form example in a case in which an ultrasound image U1 and a puncture region map M are displayed in a sub-window. The ultrasound image U1 is an image in which the portion of the thrombus BC is extracted from the ultrasound image U. For example, the determination unit 38 generates the ultrasound image U1 by cutting out the abnormal portion from the detected ultrasound image U and displays the ultrasound image U1 on the display unit 40 as the sub-window. By displaying the ultrasound image U1 in this way, the user can check a status of the thrombus BC, and thus it can be useful for the treatment of the thrombus BC.

On the other hand, the puncture region map M is a map that clearly shows the scanning region or the abnormal portion. The puncture region map M includes scanning region information 96 indicating the scanning region and abnormal portion information 98 indicating the abnormal portion. For example, the determination unit 38 acquires a puncture part schematic diagram 94 by specifying the puncture part, such as the right lower limb or the upper left arm, which is input by using the imaging menu or the input I/F unit 56 by the user. The determination unit 38 provides the scanning region information 96 on the acquired puncture part schematic diagram 94 based on the detected position of the ultrasound probe 10, and provides the abnormal portion information 98 based on the detected position of the abnormal portion. As a result, the user can more clearly and intuitively recognize the appropriate region for the puncture, in other words, the inappropriate region for the puncture. It should be noted that a form may be adopted in which the display unit 40 that displays the puncture region map M is the head mounted display worn by the user and the scanning region information 96 and the abnormal portion information 98 are displayed on the body surface of the actual subject instead of the puncture part schematic diagram 94. For example, a form may be adopted in which a visual field image including the ultrasound probe 10 is acquired by the imaging apparatus provided in the head mounted display, an operation position by the ultrasound probe 10 is detected by analyzing the visual field image, and the scanned region is displayed as the scanning region information 96 on the body surface of the subject.

It should be noted that, in each form described above, although the form has been described in which the vein BV is punctured, a form may be adopted in which the artery is punctured. In this case, since the blood flow of the blood vessel B, which is the artery, goes from the center side to the periphery side, the center side with respect to the abnormal portion at which the thrombus BC occurs need only be set as the position inappropriate for the puncture, and the periphery side with respect to the abnormal portion need only be set as the position inappropriate for the puncture.

In addition, in each form described above, the case has been specifically described in which the abnormality that occurs in the vein BV is the thrombus BC, but the same form can be adopted to a case in which the abnormality is caused by the shunt or the like as described above.

In addition, in each form described above, the form has been described in which the body part 12 is an example of the information processing apparatus according to the present disclosure, but a device other than the body part 12 may have the function of the information processing apparatus according to the present disclosure. In other words, a device other than the body part 12, for example, the ultrasound probe 10 or an external device may have a part or all of the functions of the acquisition unit 34, the detection unit 36, and the determination unit 38.

In addition, in each form described above, the body part 12 is provided with the image generation unit 32 that generates the ultrasound image U based on the sound ray signal, but the image generation unit 32 may be provided in the ultrasound probe 10 instead of the configuration described above. In this case, the ultrasound probe 10 generates the ultrasound image U and outputs the ultrasound image U to the body part 12. The CPU 50A of the control unit 50 of the body part 12 performs the puncture assist processing or the like based on the ultrasound image U input from the ultrasound probe 10.

In addition, in the form described above, the form has been described in which the body part 12 comprises the display unit 40, the input I/F unit 56, and the ultrasound probe 10, but the display unit 40, the input I/F unit 56, the ultrasound probe 10, and the control unit 50 may be indirectly connected via the network.

Figure 13:
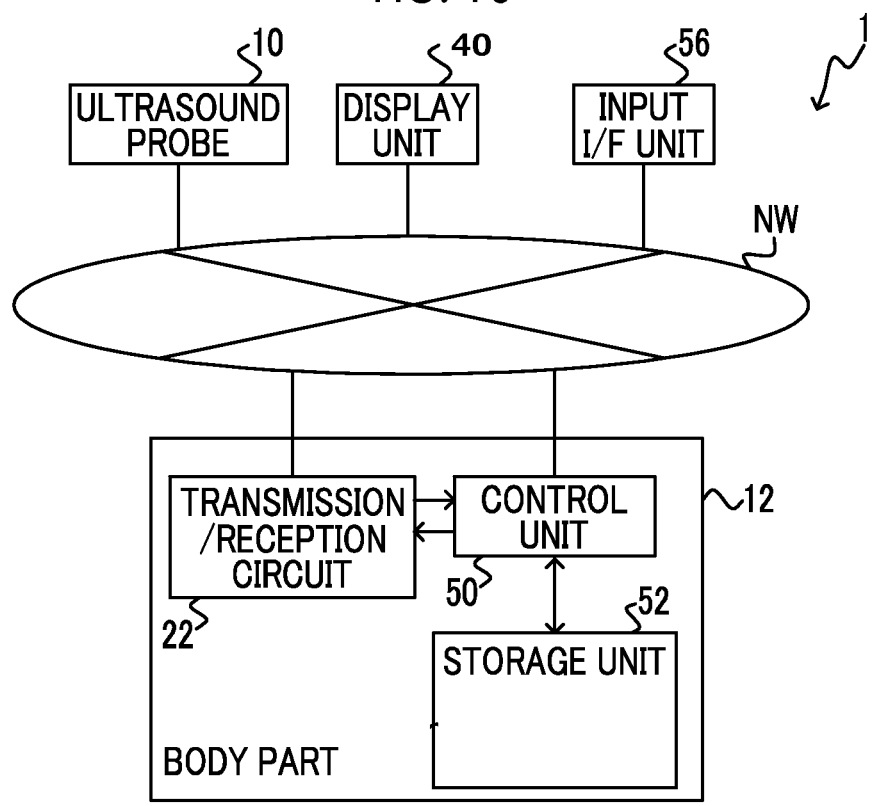
FIG. 13 is a diagram showing an example of an overall configuration of a modification example of the ultrasound diagnostic apparatus.

As an example, in the ultrasound diagnostic apparatus 1 shown in FIG. 13, the display unit 40, the input I/F unit 56, and the ultrasound probe 10 are connected to the body part 12 through a network NW. The body part 12 is obtained by removing the display unit 40 and the input I/F unit 56 from the body part 12 according to the form described above shown in FIG. 1 and adding the transmission/reception circuit 22, and comprises the transmission/reception circuit 22, the control unit 50, and the storage unit 52. The ultrasound probe 10 is obtained by removing the transmission/reception circuit 22 from the ultrasound probe 10 according to the form described above shown in FIG. 1.

As described above, in the ultrasound diagnostic apparatus 1 shown in FIG. 13, since the display unit 40, the input I/F unit 56, and the ultrasound probe 10 are connected to the body part 12 through the network NW, the body part 12 can be used as a so-called remote server. As a result, for example, the user can prepare the display unit 40, the input I/F unit 56, and the ultrasound probe 10 at the user's hand, and thus the convenience is improved. In addition, by configuring the display unit 40 and the input I/F unit 56 with the portable terminal, such as the smartphone or the tablet terminal, the convenience is further improved.

Figure 14:
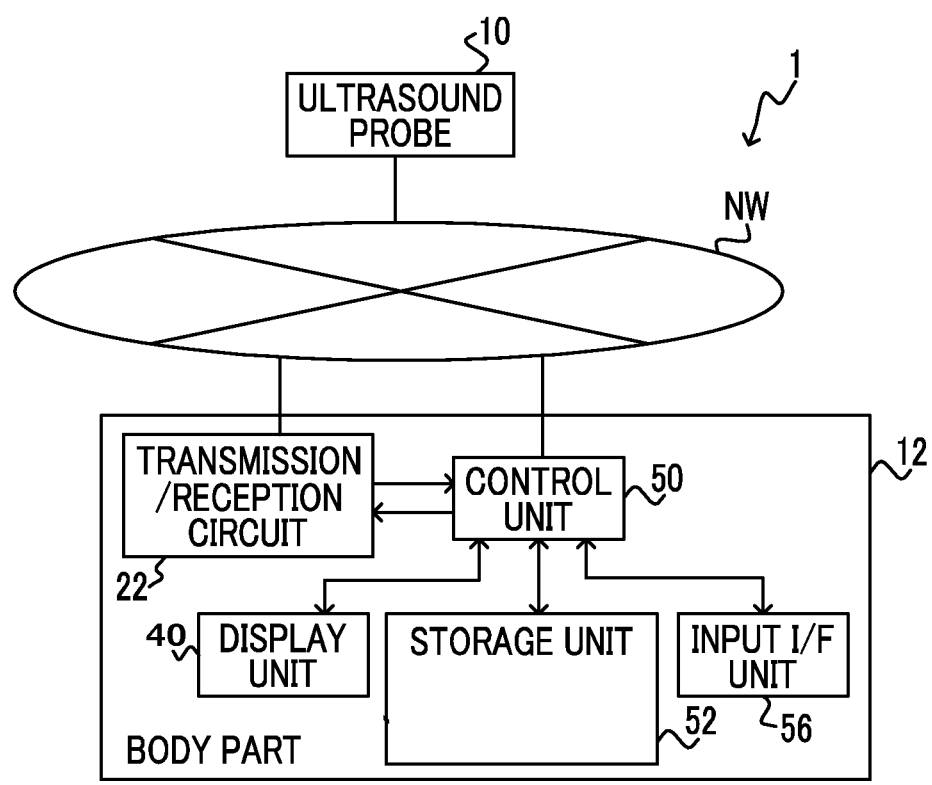
FIG. 14 is a diagram showing an example of an overall configuration of another modification example of the ultrasound diagnostic apparatus.

As another example, in the ultrasound diagnostic apparatus 1 shown in FIG. 14, the body part 12 comprises the display unit 40 and the input I/F unit 56, and the ultrasound probe 10 is connected to the body part 12 through the network NW. In this case, the body part 12 may be configured by the remote server. In addition, the body part 12 can also be configured by the portable terminal, such as the smartphone or the tablet terminal.

In addition, in the form described above, various processors shown below can be used as the hardware structure of processing units that execute various types of processing, such as the acquisition unit 34, the detection unit 36, and the determination unit 38. As described above, the various processors include, in addition to the CPU that is a general-purpose processor which executes software (program) and functions as various processing units, a programmable logic device (PLD) that is a processor of which a circuit configuration can be changed after manufacture, such as a field programmable gate array (FPGA), and a dedicated electric circuit that is a processor having a circuit configuration which is designed for exclusive use in order to execute specific processing, such as an application specific integrated circuit (ASIC).

One processing unit may be configured by one of the various processors, or may be configured by a combination of two or more processors of the same type or different types (for example, a combination of a plurality of FPGAs or a combination of the CPU and the FPGA). Also, a plurality of processing units may be configured by one processor.

A first example of the configuration in which the plurality of processing units are configured by one processor is a form in which, as represented by computers, such as a client and a server, one processor is configured by a combination of one or more CPUs and the software and this processor functions as the plurality of processing units. Second, there is a form in which, as represented by a system on chip (SoC) or the like, a processor that realizes the function of the entire system including the plurality of processing units by one integrated circuit (IC) chip is used. As described above, as the hardware structure, the various processing units are configured by using one or more of the various processors described above.

Further, more specifically, an electric circuit (circuitry) in which circuit elements, such as semiconductor elements, are combined can be used as the hardware structure of the various processors.

In addition, in the embodiment described above, the aspect has been described in which the puncture assist processing program 51 is stored (installed) in the ROM 50B in advance, but the present invention is not limited to this. Each of the puncture assist processing program 51 may be provided in a form of being recorded in a recording medium, such as a compact disc read only memory (CD-ROM), a digital versatile disc read only memory (DVD-ROM), and a universal serial bus (USB) memory. In addition, a form may be adopted in which each of the puncture assist processing program 51 is provided in a form being downloaded from an external device through a network.

From the above description, the technology described in the following supplementary notes 1 to 7 can be grasped.

[Supplementary Note 1]

An information processing apparatus comprising at least one processor, in which the processor acquires an ultrasound image of a vein in a predetermined region from a center to a periphery of a subject, detects an abnormal portion at which an abnormality occurs in the vein from the acquired ultrasound image, and determines whether a puncture in the vein is appropriate or inappropriate according to the detected abnormal portion and outputs a determination result.

[Supplementary Note 2]

The information processing apparatus according to Supplementary Note 1, in which the processor determines that a puncture at a position on a periphery side with respect to the abnormal portion is inappropriate.

[Supplementary Note 3]

The information processing apparatus according to Supplementary Note 1 or 2, in which, in a case in which a plurality of the abnormal portions are detected, the processor determines that a puncture at a position on a periphery side with respect to an abnormal portion positioned on a most center side is inappropriate.

[Supplementary Note 4]

The information processing apparatus according to any one of Supplementary Notes 1 to 3, in which the processor further acquires a position of an ultrasound probe in a case in which the acquired ultrasound image is captured, and determines whether the puncture is appropriate or inappropriate based on a detection result and the position of the ultrasound probe.

[Supplementary Note 5]

The information processing apparatus according to any one of Supplementary Notes 1 to 4, in which the processor outputs information indicating a warning as the determination result.

[Supplementary Note 6]

The information processing apparatus according to any one of Supplementary Notes 1 to 5, in which the processor detects the vein from the ultrasound image.

[Supplementary Note 7]

An information processing apparatus comprising at least one processor, in which the processor acquires an ultrasound image of a blood vessel in a predetermined region from a center to a terminal of a subject, detects an abnormal portion at which an abnormality occurs in the blood vessel from the acquired ultrasound image, and determines that a puncture of the blood vessel at a position at which a blood flow is upstream of the detected abnormal portion is inappropriate, and outputs a determination result.

The disclosure of JP2020-197656 filed on Nov. 27, 2020 is incorporated in the present specification by reference in its entirety.

All documents, patent applications, and technical standards described in the present specification are incorporated in the present specification by reference to the same extent as a case in which each document, patent application, and technical standard are specifically and individually described to be incorporated by reference.

What is claimed is:

1. An information processing apparatus comprising:
   a memory; and
   a processor coupled to the memory, the processor configured to:
   acquire an ultrasound image by capturing a vein in a predetermined region from a center to a periphery of a subject with an ultrasound probe;
   detect an abnormal portion at which an abnormality occurs in the vein from the acquired ultrasound image;
   determine whether a puncture in the vein is appropriate or inappropriate according to the detected abnormal portion, and output a determination result on a display,
   wherein the abnormal portion is a portion at which a thrombus forms;
   determine that a puncture at a position on a periphery side with respect to the abnormal portion is inappropriate in order to prevent the thrombus from exfoliating and reaching a circulatory organ; and
   output information indicating a warning included in the determination result, wherein
   the determination result includes at least an image of a vein to be punctured, and
   the information indicating the warning is information, in the image of the vein to be punctured, that allows recognition of abnormalities in the vein on the center side.

2. The information processing apparatus according to claim 1,
   wherein, in a case in which a plurality of the abnormal portions are detected, the processor is configured to determine that a puncture at a position on a periphery side with respect to an abnormal portion positioned on a most center side is inappropriate.

3. The information processing apparatus according to claim 1,
   wherein the processor is configured to:
   further acquire a position of the ultrasound probe in a case in which the acquired ultrasound image is captured, and
   determine whether the puncture is appropriate or inappropriate based on a detection result and the position of the ultrasound probe.

4. The information processing apparatus according to claim 1,
   wherein the processor is configured to detect the vein from the ultrasound image.

5. An information processing apparatus comprising:
   a memory; and
   a processor coupled to the memory, the processor configured to:
   acquire an ultrasound image by capturing a blood vessel in a predetermined region from a center to a terminal of a subject with an ultrasound probe;
   detect an abnormal portion at which an abnormality occurs in the blood vessel from the acquired ultrasound image;
   determine that a puncture of the blood vessel at a position at which a blood flow is upstream of the detected abnormal portion is inappropriate, and output a determination result on a display,
   wherein the abnormal portion is a portion at which a thrombus forms;
   determine that a puncture at a position on a periphery side with respect to the abnormal portion is inappropriate in order to prevent the thrombus from exfoliating and reaching a circulatory organ; and
   output information indicating a warning included in the determination result, wherein
   the determination result includes at least an image of a vein to be punctured, and
   the information indicating the warning is information, in the image of the vein to be punctured, that allows recognition of abnormalities in the vein on the center side.

6. An ultrasound diagnostic apparatus comprising:
   the information processing apparatus according to claim 1; and
   the ultrasound probe that is configured to receive an ultrasound echo from transmitted ultrasound, and output a reception signal based on the received ultrasound echo, wherein the processor is configured to generate an ultrasound image based on the reception signal input from the ultrasound probe.

* * * * *